United States Patent
Holmgren et al.

(10) Patent No.: US 6,558,678 B1
(45) Date of Patent: May 6, 2003

(54) **PREPARATION AND USE OF FORMALIN-KILLED COLONIZATION-FACTOR-ANTIGEN (CFA)-EXPRESSING *E. COLI* ORGANISMS FOR VACCINATION AGAINST ENTERIC INFECTION/DIARRHEA CAUSED BY ENTEROTOXIGENIC *E. COLI* BACTERIA IN HUMANS**

(76) Inventors: Jan Holmgren, Korvettgatan 1D, Västra Frölunda S-421 74 (SE); Ann-Mari Svennerholm, Korvettgatan 1D, Västra Frölunda S-421 74 (SE)

( * ) Notice: Subject to any disclaimer, the term of this patent is extended or adjusted under 35 U.S.C. 154(b) by 0 days.

(21) Appl. No.: 08/108,606

(22) PCT Filed: Feb. 25, 1992

(86) PCT No.: PCT/SE92/00110

§ 371 (c)(1),
(2), (4) Date: Nov. 8, 1993

(87) PCT Pub. No.: WO92/14487

PCT Pub. Date: Sep. 3, 1992

(30) Foreign Application Priority Data

Feb. 26, 1991 (SE) ................................................ 9100556

(51) Int. Cl.$^7$ ............................................ A61K 39/108
(52) U.S. Cl. ................................ 424/257.1; 424/200.1; 435/252.33; 435/238; 435/849; 435/252.1
(58) Field of Search ........................... 424/257.1, 200.1; 435/252.33, 238, 849, 252.1

(56) References Cited

U.S. PATENT DOCUMENTS 4,338,298 A * 7/1982 Myers .......................... 424/92
5,935,838 A * 8/1999 Askelof et al. .......... 435/252.1

FOREIGN PATENT DOCUMENTS

| DE | 1208038 | 12/1965 |
| DE | 62894 | 7/1968 |
| EP | 0255755 | 2/1988 |
| GB | 1472624 | 5/1977 |
| WO | WO 87/04604 | 8/1987 |

OTHER PUBLICATIONS

Masihi Et Al J Immunopharmac 8(3):339–345, 1986.*
Ruitte Et Al, *Immunology* 3$^{rd}$ ed Mosby, St. Louis 1993 pp 15.17–15.18.*
Evans Et Al, FEMS Microbiol Immunol 47): 9–18, 1988.*
Evans Et Al, FEMS Microbiol Immunol 1(3): 117–25, 1988.*
Evans Et Al, Gastroenterology 87(4): 934–40, 1984.*
Soderlind Et Al, Infect. Immun 36(3): 900–906, 1982.*
Gregory Et Al, Am J Vet Res 44(1): 2073–2077, 1983.*
Ahren Et Al, Infect Immun 38(1): 74–79, 1982.*
Svenne–holm Et Al, Vaccine 7(3) 196–198, 1989.*
Evans Et Al, Infect. Immun 18(2): 330–337, 1977.*
Evans et al Infect Immun 8(5): 725–730, 1973.*

* cited by examiner

*Primary Examiner*—Lynette R. F. Smith
*Assistant Examiner*—Ginny Allen Portner
(74) *Attorney, Agent, or Firm*—Darby & Darby

(57) ABSTRACT

Disclosed is a method of producing a vaccine composition against enteric infection caused by enterotoxigenic *E. coli* bacteria in humans. *E. coli* strains selected from different known strains each having the ability of expressing a certain type of colonization factor antigens are grown in a liquid culture medium. Finally formalin-killed *E. coli* strain having substantially preserved antigenic and hemagglutinating properties of said certain type of colonization factor antigens, is mixed with a pharmaceutically acceptable excipient and/or diluent. Further disclosed is a method of preventing an enteric infection caused by enterotoxigenic *E. coli* bacteria in humans, whereby a vaccine composition comprising inactivated *E. coli* strain is administered to a human being for the prevention of said infection.

7 Claims, 1 Drawing Sheet

PREPARATION AND USE OF FORMALIN-KILLED COLONIZATION-FACTOR-ANTIGEN (CFA)-EXPRESSING E. COLI ORGANISMS FOR VACCINATION AGAINST ENTERIC INFECTION/DIARRHEA CAUSED BY ENTEROTOXIGENIC E. COLI BACTERIA IN HUMANS

The present invention relates to the preparation and use of formalin-killed colonization-factor-antigen (CFA)-expressing E. coli organisms for vaccination against enteric infection/diarrhea caused by enterotoxigenic E. coli bacteria in humans.

Specially, the invention relates to a method of producing a vaccine composition against enteric infection caused by enterotoxigenic E. coli bacteria in humans, and a method of preventing an enteric infection caused by enterotoxigenic E. coli bacteria in humans.

BACKGROUND

Diarrhea caused by enterotoxinogenic *Escherichia coli* (ETEC) is an important health problem, particularly in developing countries and in travellers to these areas. In hospital- and clinic-based studies of acute diarrhea in developing countries ETEC has been identified in 10–50% of the cases, the average being ca 20% in children less than 5 years, and slightly higher in older age groups. Likewise, ETEC has been identified as the causative agent in at least one third to one half of cases of acute diarrhea among persons travelling from industrialized to developing countries.

The illness caused by ETEC ranges from mild diarrhea without dehydration to cholera-like disease. In the first 5 years of life many children in developing countries suffer from 1–2 episodes of diarrhea caused by ETEC each year. Although in the majority of ETEC infections symptoms are relatively mild, ETEC accounts for more than one billion diarrheal episodes and one million deaths annually among children in developing countries. Thus, any interventions that could reduce ETEC mortality and morbidity even partially might be of great public health significance.

No vaccine for use in humans against ETEC diarrhea is yet available. However, in a large field trial of a newly developed oral cholera vaccine it was found that the B subunit component of this vaccine, which cross-reacts immunologically with the heat-labile enterotoxin (LT) of ETEC, afforded significant protection not only against cholera but also against diarrhea caused by LT-producing ETEC. The protection against ETEC infection was particularly pronounced against illness associated with severe, life-threatening dehydration which was reduced by 86% by the vaccine during the first three months after immunization.

MECHANISMS OF DISEASE AND IMMUNITY. To cause disease, ETEC must be able to colonize the small intestine, and to elaborate LT and/or a heat-stable enterotoxin (ST, STa). E. coli LT is similar to cholera toxin in structure and function, consisting of a toxin-active A subunit attached to five B subunits that mediate binding to cell membrane receptors. The ST molecule is a small polypeptide of only 19 amino acid residues, that stimulates guanylate cyclase activity in intestinal cells. Different from LT which is a strong immunogen, ST is non-immunogenic unless experimentally conjugated to a larger carrier protein. ST-only and LT/ST-producing strains are important causes of diarrhea in endemic areas, whereas LT-only strains frequently cause disease in travellers to developing countries. The proportion of ETEC strains with different enterotoxin profiles varies from country to country.

In many ETEC strains adhesion to intestinal mucosa is mediated by antigenically distinct fimbriae. In strains pathogenic for man three main adhesins have been identified; they are referred to as colonization factor antigens CFA/I, CFA/II, and CFA/IV (formerly called PCF8775). CFA/I is a single homogenous fimbrial antigen whereas CFA/II comprises the *coli* surface (CS) antigens CS1, CS2 and CS3, and CFA/IV the CS4, CS5 and C6 antigens. Although the prevalence of these different colonization factors varies geographically, CFA/I, CFA/II or CFA/IV are usually found on one-half to three-quarters of ETEC isolated from cases with clinically significant diarrhea. However, additional adhesins are also likely to be identified.

The highest ETEC infection rates in endemic areas are seen in young children. The findings of a decreased attack rate with increasing age and of a higher proportion of asymptomatic cases in adults than in children suggest that naturally acquired protective immunity may develop. Similarly, a degree of resistance against ETEC diarrhea develops among travellers during prolonged residence in high-risk countries. Experimental studies in animals and human volunteers have also shown that ETEC infection may give rise to substantial immunity against rechallenge with the homologous organisms.

There is evidence that both antibacterial and antitoxic immunity contributes to protection against ETEC diarrhea. Antibacterial immunity against ETEC may to a large extent be ascribed to immunity against the different colonization factor antigens (CFA), even though antibodies against O-antigen may play a role as well for protection against ETEC of homologous O-gruoups. In animals, anti-CFA antibodies have protected against challenge with ETEC expressing the homologous CFAS. similarly, in both animals and human volunteers oral or intraintestinal immunization with ETEC strains expressing CFA/I, CFA/II or CFA/IV has induced protective immunity against subsequent challenge with E. coli carrying the homologous CFA/CS-factor.

Naturally induced antitoxic ETEC immunity is only directed against LT since native ST is not immunogenic. The anti-LT immune response is mainly against the B subunit portion of the molecule, which cross-reacts immunologically with the B subunits of cholera toxin. This explains why, as mentioned, oral immunization with cholera B subunit could induce protection against ETEC diarrhea [1]; interestingly protection was induced not only against LT-only but also against LT/ST ETEC strains [1]; a finding also supported by findings in animals after immunization with either cholera or LT B subunits (unpublished data).

It is also known that in humans clinical ETEC disease evokes significant antitoxic as well as antibacterial immune responses in the intestine resulting in specific IgA antibody titer increases in intestinal lavage fluid against LT and homologous CFA and O antigens [2]. Both anti-enterotoxin and anti-colonization factor antibodies can independent of each other protect against experimental ETEC infection and, when being present together in the intestine, these antibody specificities have been found to cooperate synergistically in protecting against ETEC disease [3].

In contrast to the well-established protective function of anti-LT immunity against ETEC disease, the significance of anti-ST immunity for protection remains undefined. Although ST in its natural state is not immunogenic it may give rise to ST-neutralizing antibodies when being used coupled to a carrier protein. This suggests that also vaccine-induced anti-ST immunity may be an attainable goal. However, different ST-carrier conjugates tested to date, derived either by chemical coupling or recombinant DNA techniques, have all retained significant, though sometimes reduced toxic activity. Therefore, several synthetic modified ST-peptides have been prepared recently in an attempt to identify nontoxic ST-related epitopes. Synthetic oligonucleotides encoding for similar peptides have also been made and fused to the gene for cholera B-subunit and when inserted into Vibrio cholerae these chimeric genes encode production of high concentrations of completely nontoxic ST-B subunit fusion protein. Immunization of experimental animals with such chemically derived or genetically engineered nontoxic peptide-B-subunit conjugates has evoked anti-ST antibody responses but so far with only weak neutralizing activity.

CANDIDATE VACCINES. Based on this knowledge about the key protective antigens of ETEC bacteria and of the main immune mechanisms operating against ETEC infections, it may be concluded that an effective ETEC vaccine should be given orally and ideally evoke both anti-colonization and antitoxic immune responses in the intestine. Thus, the vaccine should contain a combination of bacterial cell- and toxin-derived antigens. Different live or inactivated ETEC vaccine candidates have recently been considered based on these premises.

Live vaccines. Live bacteria expressing the major CFAs and producing B subunit or a related enterotoxoid may be considered since such a vaccine through multiplication in the gut might provide a sustained antigen stimulation of the local intestinal immune system. However, since the different colonization factors are normally not expressed on the same strains and it has not been possible to clone the genes for different CFAs into the same host organism, such vaccines must—at least for the present moment—be based on a mixture of several different strains. There are several problems, however, with this kind of vaccine approach. Among these are the risk for overgrowth of one of the included vaccine strains with suppression of the others; reversion to toxicity by uptake of toxin-encoding plasmids; low production of enterotoxoid during growth in vivo; and poor survival of the vaccine strains during storage. Therefore live oral ETEC vaccines are not yet in sight.

Non-living vaccines. The most important of the somatic antigens to be included in a vaccine are those CFAs that have a high prevalence on ETEC strains in different geographic areas. These antigens include CFA/I, CFA/II and CFA/IV and possibly a few additional CFAs as yet to be defined. However, purified CFA antigens may be relatively expensive to prepare and, furthermore, after oral administration isolated CFAs have proved to be sensitive to degradation in the human gastrointestinal tract [4, 5].

A more practical way to construct a vaccine may be to prepare killed ETEC bacteria that express the most important CFAs on their surface and combine these organisms with an appropriate toxoid component. Important vaccine preparation problems to overcome would be to (a) find a procedure that would safely kill the vaccine strains while still preserving the antigenic and adhesive (hemagglutinating) properties of different CFAs (ideally this procedure should also stabilize the CFAs against degradation in the human intestinal milieu), and (b) find conditions allowing high-level expression of CFAs on bacteria during growth in liquid medium in a fermentor in order to facilitate large-scale vaccine production.

A well-known and therefore advantageous method to inactivate bacteria for use as whole cell vaccines would be the use of formalin treatment. Usually a formalin concentration of 1 M is used for such purposes. We found that treatment of CFA expressing ETEC with commonly used vaccine preparation methods safely killed the ETEC organisms but that it at the same time destroyed most or all of the CFA antigen content and therefore these methods were not well suited for preparation of inactivated ETEC strains with retained CFA immunogenicity. In accordance with this, Levine [6] has described the limited success of Tacket et al. to use formalin-treated ETEC organisms of one strain for stimulating IgA antibody formation and protection in human volunteers. The vaccine was prepared from $E.\ coli$ strain E1392-75-2A, an O6:H16 biotype A strain that expresses CS1 and CS3 fimbriae, but does not elaborate LT or ST. When used previously as a live oral vaccine, a single dose of E1392-75-2A provided significant protection to volunteers against experimental challenge with an $LT^+/ST^+$ ETEC strain of serotype 0139:H28 that expresses CS1 and CS3. (The E1392-75-2A bacteria were formalin-inactivated by investigators at the U.S. Army Vaccine Production Facility of the Walter Reed Army Institute of Research at Forest Glen, Md.). Three doses of vaccine (each containing $5\times10^{10}$ inactivated bacteria) with $NaHCO_3$ were given by Tacket et al. at two-week intervals to nine volunteers. Significant rises in CFA antibody were detected in serum in two of nine vaccinees, whereas four of nine had detectable rises in intestinal SIgA anti-fimbrial antibody. A small challenge study was carried out in which four of the vaccinees and ten controls were challenged with pathogenic ETEC strain E24377A (0139:H28, CS1, CS3, $LT^+/ST^+$). No evidence of protection was detected: diarrhea occurred in two of four vaccinees and in six of ten controls.

With regard to expression of CFAs in liquid medium this has not been reported. Indeed, until now such expression has not been regarded possible since liquid medium is known to suppress expression of CFAs and instead induce expression of mannose-sensitive type 1 pili [7].

Initial efforts to develop prototype vaccines based on ETEC expressing different CFAs and Cs proteins [8] had to rely on growing the organisms on solid agar plates which seriously impedes the possibility for larger-scale vaccine production. In the present invention we have now developed a procedure which allows equally good expression of CFAs on ETEC during growth in liquid medium in shake culture as under optimal CFA-promoting agar plate growth conditions and we also show high-level expression of CFAs on $E.\ coli$ during fermentor cultivation conditions. We also describe a procedure by which these liquid medium fermentor-grown $E.\ coli$ are inactivated with formalin in a way which ensures safe killing of the tested ETEC vaccine strains and at the same time both preserves and stabilizes the CFAs on the bacterial surface in a defined quantifiable manner.

DESCRIPTION OF THE DRAWING

Legend to FIG. 1:

Swedish adult volunteers received three immunizations (↓)with the prototype ETEC vaccine on days 0, 14 and 28 and intestinal lavage specimens were collected immediately before and then 9 days after the second and third immunization. ELISA IgA titers against purified CFA/I, CFA/II (CS1+CS3) and CTB (GM1-ELISA) were determined and divided by the total IgA concentration of each specimen.

DESCRIPTION OF THE INVENTION

Figure 1:
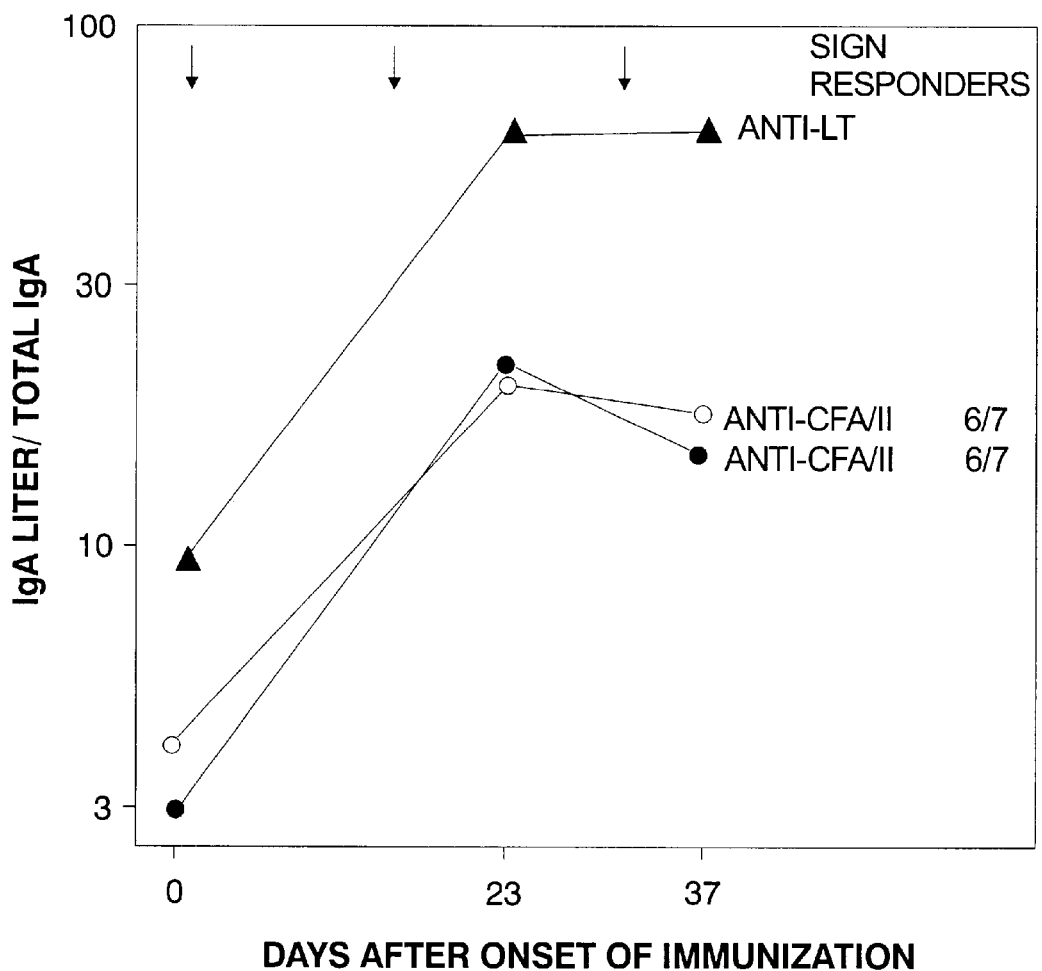

One aspect of the invention is directed to a method of producing a vaccine composition against enteric infection caused by enterotoxigenic E. coli bacteria in humans. In the method at least one E. coli strain selected from different known strains each having the ability of expressing a certain type of colonization factor antigens, is grown under appropriate conditions in a liquid culture medium allowing high-level expression of said certain type of colonization factor antigens on the surface of the E. coli bacteria, to a predetermined density, followed by harvesting and resuspension of the bacterial culture in saline, whereupon formalin is added to the suspension under slight agitation to a final concentration of 0.2 M formaldehyde, followed by incubation under continuous agitation at 37° C. for approximatly 2 hours, followed by incubation at 4° C. for 24–48 hours, resulting in a formalin-killed E. coli strain having substantially preserved antigenic and hemagglutinating properties of said certain type of colonization factor antigens, thereupon said formalin-killed E. coli bacteria are mixed with a pharmaceutically acceptable excipient and/or diluent to an appropriate concentration.

In an embodiment of this aspect of the invention said liquid culture medium comprises 1% (w/v) casamino acids, 0.15% (w/v) yeast extract, 0.4 mM $MgSO_4$, 0.04 mM $MnCl_2$, and deionized water at pH 7.4, and the cultivation is conducted with vigorous agitation or other means for accomplishing extensive aeration at approximately 37° C. for at least 4–6 hours before harvesting of the bacteria is effected by centrifugation or filtration or other means.

In an other embodiment of this aspect of the invention said strains expressing certain types of colonization factor antigens are selected from the human-intestine colonization factor antigens CFA/I, CFA/II (CS1, CS2, CS3) and CFA/IV (CS4, CS5, CS6).

In a further embodiment of this aspect of the invention there is additionally added an acid-neutralizing buffer and optionally additional antigenic components inducing immunity against for instance endotoxins.

Another aspect of the invention is directed to a method of preventing an enteric infection caused by enterotoxigenic E. coli bacteria in humans, whereby an appropriate amount of a vaccine composition comprising, as an immunizing component, at least one inactivated E. coli strain selected from different known strains each having the ability of expressing a certain type of colonization factor antigens and each having substantially preserved antigenic and hemagglutinating properties of said certain type of colonization factor antigens, is administered to a human being for the prevention of said infection.

In a preferred embodiment of this aspect of the invention the administration route is oral.

Procedures are described whereby with the aid of a fermentor selected E. coli bacterial strains can be grown to high densities in liquid medium without loss in the ability to express different CFAs including CFA/I, CFA/II and CFA/IV, and then be treated by means that safely kill the organisms without destroying the CFAs. These procedures allow such inactivated E. coli organisms to be used as safe, non-living oral vaccines against enteric infection/diarrhea caused by enterotoxigenic E. coli bacteria in humans. The procedures for achieving these bacterial vaccine components and the methods used to document their utility as intestinal mucosal immunogens include the following:

1. A method for achieving high level expression of the desired different types of CFAs (CFA/I, CFA/II and CFA/IV) on E. coli organisms during growth in liquid medium rather than as previously described only on agar plates or other solid media.

2. Successful adaptation of this method for high-level expression of these CFAs on E. coli grown in liquid medium in a fermentor.

3. A procedure for inactivating the selected E. coli organisms with the aid of formalin with almost complete preservation of the immunological reactivity with specific antibodies and the hemagglutinating activity of the different CFAs.

4. Tests showing that immunization of rabbits with the liquid-grown formalin-treated E. coli organisms give rise to equally high titers of specific antibodies against the different CFAs as does immunization with corresponding live agar-grown bacteria.

5. Tests demonstrating that the CFAs on the formalin-treated vaccine organisms have greater stability than CFAs on untreated live bacteria when the organisms are subjected to incubation in acid buffer or human gastrointestinal juice.

6. Studies documenting that liquid-grown formalin-inactivated CFA-E. coli organisms can be given without significant side-effects to human volunteers as an oral vaccine and that administration of two or three doses of such vaccine stimulates IgA antibody formation in intestinal lavage fluid as well as appearance of specific antibody-secreting cells in the circulation against the CFAs of the vaccine.

EXAMPLES

A large number of ETEC strains expressing CFA/I, CFA/II (including strains expressing CS1, CS2 or CS3 alone, CS1+CS3 or CS2+CS3) or CFA/IV (strains expressing CS4+CS6 or CS5+CS6) were tested. These strains comprised clinical isolates obtained from different parts of the world as well as laboratory-manipulated strains and included strains representing different patterns of enterotoxin production (LT+ST, LT or ST alone, and toxin-negative derivatives). As the procedures described in the subsequent examples 1–5, to the extent tested, have been found to be valid for different strains of different CFA type or subtypes and enterotoxin profiles, the experiments and results described in the examples will be limited to representative results as achieved with a few selected strains.

Example 1

Expression of CFAs on E. coli Organisms After Growth in Liquid Medium in Shake Culture or Fermentor Previously used procedures to express CFAs on E. coli have always been based on growing the organisms on solid surfaces, usually on so-called CFA agar plates [7], since it was known that growth in liquid medium usually suppressed the expression of CFAs while facilitating the expression of type 1 (common) pili on the E. coli bacteria. To facilitate large-scale production of an ETEC vaccine we have developed procedures that would allow high-level expression of different CFAs on the surface of E. coli also under growth conditions in liquid medium (in shake cultures in flasks or in a fermentor).

After having unsuccessfully tested several different commonly used bacteriologic liquid media and culture conditions we arrived at the following procedure for achieving and documenting the required levels of expression of CFAs on, initially each of the model strains SBL101 (CFA/I), SBL102 and SBL103 (both CFA/II) after growth in a liquid medium. Then, with a slight modification in the composition of medium for expression of CS5 we also achieved good expression of CFA/IV on other strains. From the frozen seed lots of the different strains (kept in glycerol at −70° C.) platinum loop scrapings were inoculated on CFA agar plates which were inoculated at 37° C. overnight. Colonies on the plates were controlled for expression of the appropriate CFA by direct agglutination tests with specific monoclonal antibodies against CFA/I, CS1, CS2, CS3, CS4, CS5 and CS6. These monoclonal antibodies have been prepared in the laboratory of the applicants. Bacteria on the CFA agar plates were then harvested with phosphate buffered saline (PBS) and $5-10\times10^9$ organisms from this suspension were added as inoculum into 400 ml of liquid medium. The composition of this CFA medium was: Casamino Acids 1% (w/v), Yeast extract 0.15% (w/v), $MgSO_4$ 0.4 mM, $MnCl_2$ 0.04 mM, $H_2O$ deionized, pH 7.4. The flasks were incubated with shaking, 150 rev/min, for ca 20 hours at 37° C. at which time the optical density for an 1:10 dilution of the suspension was ca 0.25–0.5. The bacteria were harvested by centrifugation at +4° C., the bacterial pellet was washed once with PBS and the bacteria again sedimented by centrifugation and resuspended in PBS to yield a suspension which in dilution 1:10 had an optical density of 0.285. This suspension, and for comparison suspensions of bacteria harvested from parallel cultures of the strains on CFA agar plates adjusted to the same optical density, were tested in serial dilutions for expression of the appropriate CFA. Both direct agglutination with monoclonal anti-CFA antibody and a quantitative CFA inhibition ELISA developed in the laboratory of the applicants were used for these analyses.

The results are summarized in Table 2. They show that the suspensions obtained after growth of the organisms in flasks in the liquid medium had comparable expression of CFAs (when adjusted to the same bacterial concentration) as bacteria grown on CFA agar plates.

The plasmids in strains SBL102 and SBL103 encoding for the different CFA/II CS proteins also encoded for bacterial resistance against ampicillin and kanamycin. Therefore, parallel cultures were performed of these strains in liquid medium and in agar supplemented with these antibiotics. Although the values in table 2 are those obtained in the absence of antibiotics those obtained in the presence of antibiotics were practically identical (not shown). Likewise, the growth conditions in liquid medium that were used for the experiment described in table 2 proved equally satisfactory as growth on CFA agar plates for expression of CFA/I, CFA/II and CFA/IV (each of the subproteins CS4, CS5 and CS6) from several other strains tested; for optimal expression of CS5 both the CFA agar used for the preculture and the liquid CFA medium were supplemented with 0.15% Bacto Bile salts 1.5 g/l (Difco).

In subsequent experiments this procedure for high-level expression of CFAs on ETEC in liquid cultures was adapted to growth in liquid medium in a fermentor. The following procedure, exemplified below for a CFA/I strain, but found equally useful for other strains producing CFA/I or CFA/IV, was found to result in similar expression of CFA per number of bacteria as growth of CFA agar or in shake cultures.

CFA agar plates were inoculated with strain SBL101 (CFA/I) and grown at 37° C. over night; frozen seed lot bacteria were used as inoculum. The bacteria were harvested from the CFA agar plates with physiological saline and $5\times10^{10}$ of the bacteria were added as inoculum into 4 liters of CFA medium; a log phase shake culture of the bacteria in CFA medium could also be used as inoculum. The bacteria were then in a Bio-flo III fermentor (New Brunswick Scientific Co, Edison, N.J., USA) grown at 37° C. with vigorous agitation (800 rev/min), without adjustment of pH. Already 4–5 hours after starting the fermentor culture the optical density of the culture was 4–5, i.e. a 1:10 dilution of the suspension was 0.4–0.5. No increase in optical density was seen after continued culture in the fermentor for 20 hours. Specimens collected from the fermentor at different intervals after starting the culture—and for comparison suspensions of bacteria prepared from a shake culture (in flasks) of the same bacterial inoculum—were tested for expression of CFA/I after adjustment to the same bacterial concentration, i.e. $10^{10}$ bacteria per ml. As shown in Table 3 the expression of CFA/I (per number of bacteria), was optimal already after 4–5 hours of culture in the fermentor and comparable to the CFA/I expression seen on bacteria grown in shake cultures in flasks for 20 hours.

Example 2

A Procedure for Formalin Inactivation of E. coli Bacteria with Preservation of CFA's Immunoreactivity as Well as Hemagalutinating Activity Different physical and chemical inactivation methods including treatment with formalin under different conditions were tested with unsatisfactory results, before a suitable procedure described in this example was arrived at. This procedure, that includes mild formalin treatment at different temperatures for several days fulfilled the criteria of resulting in complete killing of putative E. coli vaccine organisms without causing significant loss in their CFA antigen content or quality. This was tested by determining the amounts of different CFAs on bacteria before and after formalin-treatment using the quantitative CFA inhibition ELISA based on monoclonal antibodies against the different CFAs/CS components as described in example 1. This method allows precise detetermations of CFAs on bacterial surfaces. The set requirements included that the bacterial preparation after killing should have retained at least one third of the CFA antigen content as compared with the live starting organisms, and also have retained detectable hemagglutinating activity, in support of retained CFA antigenicity.

The following example describes the procedure and its usefulness in further detail. Bacteria expressing either CFA/I or CFA/II/CS antigens were grown in liquid medium and suspended in PBS using the same procedures as described in example 1. Thereafter formalin (HCHO) was added to the suspension under slight agitation of the bacterial suspension to a final concentration of 0.2 M formaldehyde. The suspension was then incubated under continuous stirring at 37° C. for ca 2 hours whereafter it was transferred to a cold room and kept at 4° C. for another 24–48 hours. After completed incubation with formalin subsamples were removed and tested for the lack of viable organisms by cultivation both in broth and on agar plates; agar plates and broth flasks were inspected daily for 14 days. The procedure consistently resulted in complete killing of all the E. coli organisms tested.

After completed formalin-treatment in the cold, the bacterial suspensions were analysed for CFA content by means of studying hemagglutinating activity of the respective specimens [7] and for capacity to inhibit binding of corresponding monoclonal antibodies in CFA ELISA as described [9]. A non-treated, freshly prepared culture of the respective strain, adjusted to the same bacterial concentration as the formalin-treated organisms, was included in each experiment for comparison. As shown in Table 4 the formalin-treated preparations had retained hemagglutinating ability and had at least 50% retained CFA antigenicity as assessed in the respective CFA ELISA inhibition tests. These results that the formalin-treated bacteria inhibited binding of the corresponding monoclonal antibodies to solid phase bound purified CFA by 50% in concentrations corresponding to 50–100% of those of non-treated bacteria, were verified in a number of consecutive experiments.

Example 3

Comparison of Storage/incubation Stability of CFAs on Formalinized and Untreated (live) ETEC Organisms Studies from other laboratories have shown that isolated non-treated CFA fimbriae are very sensitive to gastric acid [4, 5]. Prior neutralization of gastric acid to neutral pH did not seem to prevent its adverse effect on the CFA antigenicity of the fimbrial protein [4]. Against this background we compared the antigenicity of CFAs as expressed on untreated $E.$ $coli$ bacteria and on corresponding formalin-treated $E.$ $coli$ after incubation in acid gastrointestinal juice and jejunal fluid, respectively. Specimens were also incubated in PBS adjusted to different pHs.

In initial experiments different untreated and formalin-treated bacterial suspensions were incubated at different pH, from pH 3 to pH 11, for 30 min at 37° C. before readjustment to neutral pH. In no instance did incubation at these pHs affect the CFA antigenicity of either the untreated or formalin-treated killed bacterial preparations. In subsequent experiments incubation of live and formalin-inactivated bacteria in buffer at pH 2, in acid gastrointestinal juice and in jejunal fluid was compared. Gastrointestinal juice and jejunal fluids were collected from adult Swedes at the Sahlgrenska Hospital in Göteborg. As shown in Table 5 formalin-treated bacteria were only marginally or not at all affected by incubation in buffer at pH 2 or in acid gastrointestinal juice and no decrease in CFA antigenicity was observed after incubation in jejunal fluid. The CFA antigenicity of untreated live bacteria, on the other hand, was in most instances markedly reduced both after incubation in buffer at pH 2 and in acid gastrointestinal juice. These analyses indicate that formalin-treatment protects the CFA fimbriae from degradation in gastric juice.

Example 4

Comparison of Immunogenic Properties of CFAs on Formalinized and Untreated (live) ETEC The capacity of formalinized and untreated (live) CFA positive $E.$ $coli$ bacteria to induce anti-CFA antibody responses was compared. Adult New Zealand White rabbits weighing 2–3 kg at the onset of immunization were given 3–5 subcutaneous injections with corresponding doses ($5 \times 10^8$–$2 \times 10^9$ bacteria) of formalinized or untreated live bacteria; the initial injections were given in Freund's complete adjuvant, the second injections in incomplete adjuvant and subsequent immunizations without adjuvant. The formalinized bacteria were prepared at the onest of immunization and then stored at +4° C. until used; the live bacteria were freshly prepared on the day of each immunization. Formalinized bacteria had been cultured in CFA medium and untreated live bacteria in CFA agar; both the formalinized and the nontreated bacteria were washed twice in PBS before immunization.

Animals were bled immediately before onset of immunization and then 7–10 days after the last injection. Sera wera prepared and frozen in portions at −30° C. until analysed. Specific antibody responses against the CFA of the immunizing strain were determined using different ELISA methods. ELISA microtiter plates were coated with purified CFAs, i.e. CFA/I, CFA/II (CS1+CS3), CS2, CS4 or CS5 dissolved in PBS to a final concentration of 1–5 $\mu$g/ml, by incubating the plates with the CFA solution at 37° C. over night. Five-fold serial dilutions of sera were then titrated in the plates as previously described [2, 3]. The titers were determined as the reciprocal of the intrapolated dilution giving an absorbance of 0.3 above the background when reacting the enzyme with its substrate for 20 min.

None of the preimmunization bleedings had significant CFA antibody levels, i.e. CFA titers exceeding 50. After completed immunization, on the other hand, all sera had antibody titers against the homologous CFA varying between 25.000 and 300.000 (Table 6). Immunization with formalinized bacteria induced very similar titers against the homologous CFA as corresponding untreated organisms (Table 6).

Example 5

Tests of Formalinized ETEC for Safety and Ability to Stimulate Specific IgA Antibody Formation in Human Intestine A preparation of the ETEC vaccine consisting of formalin-killed bacteria expressing CFA/I, CS1, CS2 and CS3 (i.e. the strains SBL 101, SBL 102 and SBL 103 presented in Table 1) has been prepared by the National Bacteriological Laboratory in Sweden for small scale clinical trials. This vaccine component has been given together with cholera B subunit (CTB [1]). A study has been conducted in adult Swedish volunteers to test this combined CFA-ETEC-CTB vaccine for safety and immunogenicity locally in the gut. Antibody responses in serum as well as production of specific antibodies by peripheral blood lymphocytes have also been assessed.

Each of the volunteers received three oral immunizations with $10^{11}$ killed $E.$ $coli$ organisms and 1 mg of CTB in each two weeks apart. The vaccine was given in 150 ml of a buffered bicarbonate solution, using the same citrate-bicarbonate tablets (ACO, Stockholm, Sweden) as for the oral cholera vaccine in the field trial in Bangladesh [1]. Intestinal specimens and sera were collected immediately before and then 9 days after the second and third immunizations; peripheral blood lymphocytes were obtained on the day of the initial immunization and then 7 days after the first, the second and the third immunization.

Intestinal IgA antibody responses against the most important protective antigens were examined in intestinal lavage fluid as previously described [2]. The intestinal lavages were performed by letting the volunteers drink an isotonic salt solution (usually 3–5 liters) until a watery diarrhea ensued. The liquid stool that was collected was filtered through gauze, treated with various enzyme inactivators, centrifuged and concentrated by freeze-drying. In previous studies we have shown that intestinal lavage fluid is a rich source of locally produced secretory IgA antibodies against intestinally applied antigen; secretory IgA antibodies synthesized locally in the gut are probably of prime importance for protective immunity against ETEC diarrhea. Immunocytes stimulated locally in the gut, e.g. by an oral vaccine, usually migrate via the lymph to the blood and then return to the intestine where they mature into mainly IgA-secreting plasma cells. By collecting peripheral blood lymphocytes at a defined time early after oral vaccination—optimally on day 7 [10]—these intestinal antibody secreting cells (ASCs) can be obtained and analysed for production of specific antibodies against the antigens used for stimulation. Finally, to a lesser degree serum antibodies of particularly IgA class may also reflect such intestinal immune responses.

Twenty-six volunteers received three doses of the vaccine. In no instance were any local or systemic adverse reactions that could be associated with the immunization noted. Intestinal lavage fluids that were collected from 11 of the vaccinees were examined for antibodies against CTB/LT, CFA/I, CFA/II and the O-antigen of one of the immunizing strains [2]. Specific ELISA IgA titers divided by the total IgA content of each specimen were determined. As shown in Table 7 significant IgA antibody responses, were observed against CFA/I, and CFA/II as well as against CTB in most of the vaccinees. The frequency of responses in intestine was comparable to that previously observed in Bangladeshis convalescing from infection with CFA-positive E. coli. The magnitudes of the antibody responses against CFA/I and CFA/II were comparable (FIG. 1) with those previously seen in Bangladeshi convalescents from ETEC disease. The volunteers also responded with marked intestinal IgA antibody responses to the CTB component of the vaccine (FIG. 1) and these responses were higher than the anti-LT responses observed after clinical ETEC disease.

These results show that the ETEC vaccine was capable of inducing substantial CFA antibody responses locally in the intestine; such responses have previously been difficult to induce in humans by oral immunization with isolated fimbriae [4, 5]. The immunization also resulted in the appearance of specific ASCs in the blood as determined with an ELISPOT assay [10] against CFA/I, CFA/II and LT/CTB in most of the vaccinees (Table 7). Elevated numbers of anti-CFA ASCs were noticed already after a single dose of the vaccine. The responses of CFA antibody producing cells were only slightly higher after the second and third dose than after the initial immunization whereas optimal numbers of anti-LT producing cells were found after the second immunization. The anti-CFA antibodies produced were predominantly of IgA class but some ASCs producing IgM were found as well; anti-CTB ASCs were predominantly of IgA isotype but some IgG producing cells were also identified. The vaccine also gave rise to significant serum antibody responses against CFAs as well as CTB/LT in most of the volunteers (Table 7)

CITED PAPERS

1. Clemens J, Sack D, Harris JR, Chakraborty J, Neogy PK, Stanton B. Huda N, Khan MU, Kay BA, Khan MR, Ansaruzzaman M, Yunus M, Rao MR, Svennerholm A-M, Holmgren J: Cross-protection by B-subunit whole cell cholera vaccine against diarrhea assosiated with heat-labile toxin-producing enterotoxigenic Escherichia coli: results of a large-scale field trial. J Infect Dis 158:372–377, 1988.
2. Stoll BJ, Svennerholm A-M, Gothefors L, Barua D, Huda S, Holmgren J: Local and systemic antibody responses to naturally acquired enterotoxigenic Escherichia coli diarrhea in an endemic area. J Infect Dis 153:527–534, 1986.
3. Åhrén C, Svennerholm A-M: Synergistic protective effect of antibodies against Escherichia coli enterotoxin and colonization factor antigens. Infect Immun 38:74–79, 1982.
4. Levine MM, Morris JG, Losonsky G, Boedeker E, Rowe B: Fimbriae (Pili) adhesins as vaccines. In Protein-Carbohydrate Interaction in Biological Systems, pp. 143–145, Academic Press, London, 1986.
5. Evans DG, Graham DY, Evans DJ Jr, Opekun A: Administration of purified colonization factor antigens (CFA/I, CFA/I) of enterotoxigenic Escherichia coli to volunteers. Response to challenge with virulent enterotoxigenic Escherichia coli. Gastroenterology 87:934–940, 1984.
6. Levine MM: Vaccines against enterotoxigenic Escherichia coli infection. In Woodrow GC, Levine MM (eds): New generation vaccines. Marcel Dekker, Inc, N.Y. 1990, p 649–660.
7. Evans DG, Evans DJ Jr: New surface associated heat-labile colonization factor antigen (CFA/II) produced by enterotoxigenic Escherichia coli or serogroups O6 and O8. Infect Immun 21:638–647, 1978.
8. Svennerholm A-M, Holmgren J, Sack DA: Development of oral vaccines against enterotoxinogenic Escherichia coli diarrhoea. Vaccine 7:196–198, 1989.
9. Lopez-Vidal Y, Klemm P, Svennerholm A-M: Monoclonal antibodies against different epitopes on colonization factor antigen I of enterotoxin-producing Escherichia coli. J Clin Microbiol 26:1967–1972, 1988.
10. Czerkinsky C, Svennerholm A-M, Quiding M, Jonsson R, Holmgren J: Antibody-producing cells in peripheral blood and salivary glands in humans. Infect Immun (in press) 1991.

TABLE 1

Properties of E. coli strains used in cited examples

| Strain designation | CFA type | Toxin pattern | Serotype | Source |
|---|---|---|---|---|
| SBL101 | CFA/I | ST$^+$,LT$^-$ | O78:H12 | Strain 325542, Göteborg, Sweden |
| SBL102 | CFA/II (CS1) | ST$^-$,LT$^-$ | O139:H28 | 60R936, M McConnell, Colindale, UK |
| SBL103 | CFA/II (C52 + CS3) | ST$^+$,LT$^-$ | O6:H16 | 58R61 Ibid |

TABLE 2

Expression of CFAs on E. coli bacteria after growth in liquid CFA medium in comparison with growth on CFA agar plates

| | | Specific CFA titer[a] with monoclonal antibodies | |
|---|---|---|---|
| Strain (CFA type) | Growth condition | Agglutination | ELISA inhibition |
| SBL101 (CFA/I) | Liquid | 1/32 | 1/40 |
| | Agar | 1/32 | 1/50 |
| SBL102 (CFA/II; CS1) | Liquid | 1/32 | 1/200 |
| | Agar | 1/32 | 1/200 |
| SBL103 (CFA/II; CS2 + CS3) | Liquid | 1/16[a] | 1/200[b] |
| | Agar | 1/16 | 1/230 |

[a] After adjustment of all cultures to $10^{10}$ bacteria/ml
[b] As assayed with anti-CS2 MAb

TABLE 3

Expression of CFAs on *E. coli* bacteria strain SBL101 (CFA/I) after growth in liquid medium in a fermentor and in a shaker, respectively

| Time of culturing | Specific CFA titer[a] | |
|---|---|---|
| (hours) | Fermentor culture | Shake culture |
| 2 | 1/80 | N.T. |
| 3 | 1/160 | 1/80 |
| 4 | 1/200 | N.T. |
| 5 | 1/250 | N.T. |
| 7 | 1/250 | 1/250 |
| 9 | 1/250 | N.T. |
| 20 | 1/250 | 1/250 |

[a] After adjustment of bacterial cultures to $10^{10}$ organisms/ml and using the CFA/I inhibition ELISA method (9).

TABLE 4

Preservation of immunoreactivity and hemagglutinating activity of CFAs on formalin-treated as compared with untreated (live) *E. coli* bacteria

| Strain (CFA/CS type) | Preparation[a] | Specific CFA titer[b] | | Hemaggl. activity[c] |
|---|---|---|---|---|
| | | CFA/I | | |
| SBL101 | F | 1/81 | | + |
| (CFA/I) | L | 1/81 | | + |
| | | CS1 | | |
| SBL102 | F | 1/243 | | + |
| (CS1) | L | 1/243 | | + |
| | | CS2 | CS3 | |
| SBL103 | F | 1/81 | 1/54 | + |
| (CS2 + CS3) | L | 1/81 | 1/81 | + |

[a] F = Formalin-inactivated bacteria; L = live, untreated bacteria.
[b] As tested by CFA inhibition ELISA with serial 3-fold dilutions of bacterial suspensions with $10^{10}$ bacteria/ml: the titers given are the last dilution causing $\leq 50\%$ inhibition of the reaction achieved in absence of bacteria.
[c] Tested by mixing 50 µl of undiluted bacterial suspensions with 1% human erthrocytes in presence of 1% w/v of D-mannose.

TABLE 5

Stability of CFAs on formalin-treated as compared with untreated (live) *E. coli* bacteria after incubation in human gastrointestinal secretions and in acid pH.

| | SBL101 | | SBL103 | | | |
|---|---|---|---|---|---|---|
| Incubated in | F[a] | L[a] | F | L | F | L |
| | Specific CFA titer[b] (% retained CFA antigenicity[c]) | | | | | |
| | anti-CFA/I | | anti-CS2 | | anti-CS3 | |
| PBS, pH7.2 | 1/100 | 1/200 | 1/150 | 1/250 | 1/25 | 1/80 |
| PBS, pH2 | 1/75 (75%) | 1/80 (40%) | 1/100 (70%) | 1/9 (4%) | 1/15 (60%) | 1/8 (10%) |
| Acid gatro-intestinal juice | 1/50 (50%) | 1/40 (20%) | 1/125 (85%) | 1/27 (12%) | 1/25 (100%) | 1/8 (10%) |
| Jejunal fluid | 1/100 (100%) | 1/200 (100%) | 1/150 (100%) | 1/250 (100%) | 1/25 (100%) | 1/25 (35%) |

[a] F - Formalin-inactivated; L - live, untreated bacteria
[b] As tested in CFA inhibition ELISA usinq appropriate anti-CFA or anti-CS MAbs (see Table 3).
[c] In comparsion with incubation in PBS, pH7.2

TABLE 6

CFA antibody responses against formalin-treated and untreated (live) CFA positive *E. coli*.

| | | ELISA titer | |
|---|---|---|---|
| Immunization Strain (CFA/CS factors) | Antibody against | Formalinized bacteria | Untreated bacteria |
| SDL101 (CFA/I) | CFA/I | 77.000 (62.000–93.000) | 50.000 (30.000–100.000) |
| SBL102 (CS1) | CS1 | 63.000 (39.000–100.000) | |
| SBL103 (CS2 + CS3) | CS2 | 26.000 (23.000–30.000) | |
| 247425 (CS1 + CS3) | CS1 + CS3 | 250.000 | 270.000 (150.000–300.000) |
| E11881E (CS4 + CS6) | CS4 | 40.000 | 50.000 (30.000–70.000) |
| | | 30.000 | |
| E17018A(CS5 + CS6) | CS5 | 25.000 | 40.000 (20.000–70.000) |
| | | 25.000 | | a Rabbits were given 3–5 subcutaneous immunizations with $5 \times 10^8$–$2 \times 10^9$ bacteria in each.

TABLE 7

Frequency of significant IgA antibody responses in intestinal lavage, in peripheral blood lymphocytes and in serum after immunization with 3 oral doses of the prototype ETEC vaccine

| IgA antibody responses to: | Intestine[a)] | Blood ASC | Serum |
|---|---|---|---|
| CFA/I | 9/11 (82%) | 16/19 (79%) | 8/12 (75%) |
| CFA/II | 8/11 (73%) | 16/19 (84%) | 6/12 (50%) |
| CTB/LT | 9/11 (82%) | 19/19 (89%) | 11/12 (92%) |

What is claimed is:

1. A method for producing a formalin-killed *E. coli* bacterial strain for use in a vaccine against enteric infection caused by *E. coli* bacteria in humans comprising the steps of:

providing at least one *E. coli* bacterial strain expressing colonization factor antigens on the surface of said bacteria, growing said *E. coli* bacterial strain in liquid culture medium with vigorous agitation to a predetermined density, harvesting said *E. coli* bacterial strain, resuspending said harvested *E. coli* bacterial strain in saline, adding formalin to said harvested, resuspended bacterial strain to a final concentration of 0.2M formaldehyde, incubating said formalin-treated *E. coli* bacterial strain at 37° C. under conditions of continuous agitation for about 2 hours, further incubating said formalin-treated bacterial strain at 4° C. for between about 24 hours and about 48 hours, thereby obtaining a formalin-killed *E. coli* bacterial strain and, collecting said formalin-killed *E. coli* bacterial strain.

2. The method of claim 1 further comprising adding a pharmaceutically acceptable excipient or diluent.

3. The method according to claim 1, wherein said liquid culture medium comprises 1% (w/v) casamino acids, 0.15% (w/v) yeast extract, 0.4 mM $MgSo_4$, 0.04 mM $MgCl_2$, and deionized water at pH 7.4, and said growing step is conducted with vigorous agitation at about 37° C. for at least 4–6 hours before said harvesting step.

4. The method according to claim 1, wherein said *E. coli* colonization factor antigens are selected from the group consisting of human-intestine colonization factor antigens CFA/I, CFA/II and CFA/IV.

5. The method according to claim 1 further comprising adding an acid-neutralizing buffer.

6. The method of claim 1, wherein said predetermined density is about $10^{10}$ bacteria/ml.

7. A method for producing formalin-killed *E. coli* cells for use in an orally administrable vaccine against enteric infection caused by *E. coli* bacteria in humans comprising the steps of:

providing at least one *E. coli* bacterial strain expressing colonization factor antigens on the surface of said bacterial cells;

growing said cells in liquid culture medium with vigorous agitation to a density of about $10^{10}$ cells/ml, wherein the expression of said colonization factor antigens is maintained at a high level during said growth;

harvesting said cells;

resuspending said harvested cells in saline;

adding formalin to said resuspended cells to a final concentration of 0.2 M formaldehyde;

incubating said formalin-treated cells at 37° C. under conditions of continuous agitation for about 2 hours;

further incubating said formalin-treated cells at 4° C. for between about 24 hours and about 48 hours, thereby obtaining formalin-killed *E. coli* cells;

collecting said formalin-killed *E. coli* cells; and mixing said collected formalin-killed *E. coli* cells with cholera toxin β subunit.

\* \* \* \* \*